United States Patent
Wu

(10) Patent No.: US 8,625,848 B2
(45) Date of Patent: *Jan. 7, 2014

(54) ADJUSTING DISPLAY FORMAT IN ELECTRONIC DEVICE

(75) Inventor: Tung-Lin Wu, New Taipei (TW)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 176 days.

This patent is subject to a terminal disclaimer.

(21) Appl. No.: 13/327,998

(22) Filed: Dec. 16, 2011

(65) Prior Publication Data

US 2012/0243735 A1 Sep. 27, 2012

(30) Foreign Application Priority Data

Mar. 24, 2011 (TW) ............................. 100110070 A

(51) Int. Cl.
*G06K 9/00* (2006.01)
(52) U.S. Cl.
USPC ......................................................... 382/103
(58) Field of Classification Search
USPC ................. 382/103, 106, 181, 190, 298, 301; 348/63, 469, 561, 581; 708/204, 208
See application file for complete search history.

(56) References Cited

U.S. PATENT DOCUMENTS

| | | | | |
|---|---|---|---|---|
| 5,668,743 | A * | 9/1997 | Kushelvesky | 702/158 |
| 5,739,893 | A * | 4/1998 | Karasawa et al. | 351/158 |
| 7,343,026 | B2 * | 3/2008 | Niwa et al. | 382/103 |
| 8,209,635 | B2 * | 6/2012 | Thom | 715/863 |
| 8,510,462 | B2 * | 8/2013 | Riggert et al. | 709/232 |
| 2004/0160386 | A1 * | 8/2004 | Michelitsch et al. | 345/10 |
| 2007/0159470 | A1 * | 7/2007 | Jeng et al. | 345/204 |
| 2008/0199049 | A1 * | 8/2008 | Daly | 382/107 |
| 2008/0316372 | A1 * | 12/2008 | Xu et al. | 348/739 |
| 2009/0055853 | A1 * | 2/2009 | Jung et al. | 725/10 |
| 2009/0141147 | A1 * | 6/2009 | Alberts et al. | 348/240.99 |
| 2009/0169058 | A1 * | 7/2009 | Chen | 382/106 |
| 2009/0284594 | A1 * | 11/2009 | Mitsuhashi | 348/135 |
| 2010/0188426 | A1 * | 7/2010 | Ohmori et al. | 345/660 |
| 2011/0141114 | A1 * | 6/2011 | Chen et al. | 345/428 |
| 2011/0243388 | A1 * | 10/2011 | Sakaguchi et al. | 382/103 |
| 2011/0254846 | A1 * | 10/2011 | Lee et al. | 345/427 |
| 2012/0254779 | A1 * | 10/2012 | Ollivierre et al. | 715/764 |
| 2012/0287163 | A1 * | 11/2012 | Djavaherian | 345/667 |
| 2013/0029723 | A1 * | 1/2013 | Das et al. | 455/557 |

* cited by examiner

*Primary Examiner* — Jason M Repko
*Assistant Examiner* — Shervin Nakhjavan
(74) *Attorney, Agent, or Firm* — Altis Law Group, Inc.

(57) ABSTRACT

A display format adjustment system includes a receiving module, a visual condition determination module, a display format determination module, and a display control module. The receiving module receives content for display in a first display format. The visual condition determination module determines a visual condition of a viewer in front of a display. The display format determination module determines a second display format based on the first display format and the visual condition of the viewer. The display control module displays the content in the second display format on the display.

14 Claims, 4 Drawing Sheets

ADJUSTING DISPLAY FORMAT IN ELECTRONIC DEVICE

CROSS-REFERENCE TO RELATED APPLICATIONS

Relevant subject matter is disclosed in co-pending U.S. patent applications entitled "ADJUSTING PRINT FORMAT IN ELECTRONIC DEVICE", U.S. application Ser. No. 13/328,008, Filed on Dec. 26, 2011, and "ADJUSTING DISPLAY FORMAT IN ELECTRONIC DEVICE", U.S. application Ser. No. 13/328,019, Filed on Dec. 26, 2011.

BACKGROUND

1. Technical Field

The disclosure generally relates to a system and a method for adjusting display format in an electronic device.

2. Description of Related Art

Generally, a desktop computer or a mobile terminal includes a display screen for communicating with a viewer. When the font size and/or image size of the content displayed on the display screen is too small, it will be difficult for the viewer to view the content clearly. A viewer may manually scale down or scale up the text font size and/or the image size of the content to achieve an optimum viewing effect. But it's inconvenient for the viewer to adjust the display format manually. Therefore, there is a need for a technique for automatically adjusting the size of the content to enable clearer and easier viewing.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

FIG. 3 shows an example of a visual acuity test chart.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

In general, the word "module", as used herein, refers to logic embodied in hardware or firmware, or to a collection of software instructions, written in a programming language, such as, Java, C, or assembly. One or more software instructions in the modules may be embedded in firmware, such as in an EPROM. The modules described herein may be implemented as either software and/or hardware modules and may be stored in any type of non-transitory computer-readable medium or other storage device. Some non-limiting examples of non-transitory computer-readable media include CDs, DVDs, BLU-RAY, flash memory, and hard disk drives.

Figure 1:
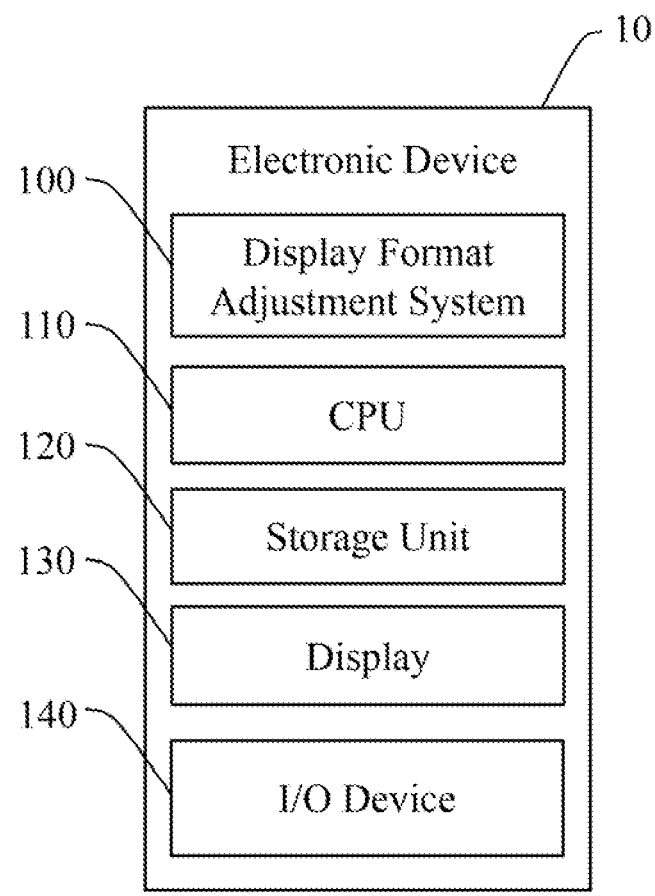
FIG. 1 is a schematic diagram of one embodiment of an electronic device suitable for use in implementing a display format adjustment system.

FIG. 1 is a schematic diagram of one embodiment of an electronic device 10. In one embodiment, the electronic device 10 includes a display format adjustment system 100, at least one central processing unit (CPU) 110, a storage unit 120, a display 130, and other I/O device(s) 140. The electronic device 10 implements the functions of the display format adjustment system 100. The electronic device 10 can be a general purpose computing device such as a desktop computer, a tablet computer, a personal digital assistant (PDA), a smart phone, or the like.

The storage unit 120 may be any form of volatile or non-volatile storage, including, for example, RAM, ROM, EPROM, flash memory, a magnetic disk such as an internal hard disk or a removable disk, an optical disk such as a CD-ROM, or any other storage device which can be used to store the desired information and which can be accessed by the display format adjustment system 100. The storage unit 120 may store machine-executable instructions, data, and various programs, such as an operating system and one or more application programs, all of which may be processed by the CPU 110. The display 130 can be a liquid crystal display (LCD) or a cathode-ray tube (CRT) display. The electronic device 10 may include one or more I/O devices 140 such as a keyboard, a mouse, a touch pad, or other pointing device. The storage unit 120, the display 130 and the other I/O devices 140 are connected to the CPU 110 through a system bus (not shown in FIG. 1).

Figure 2:
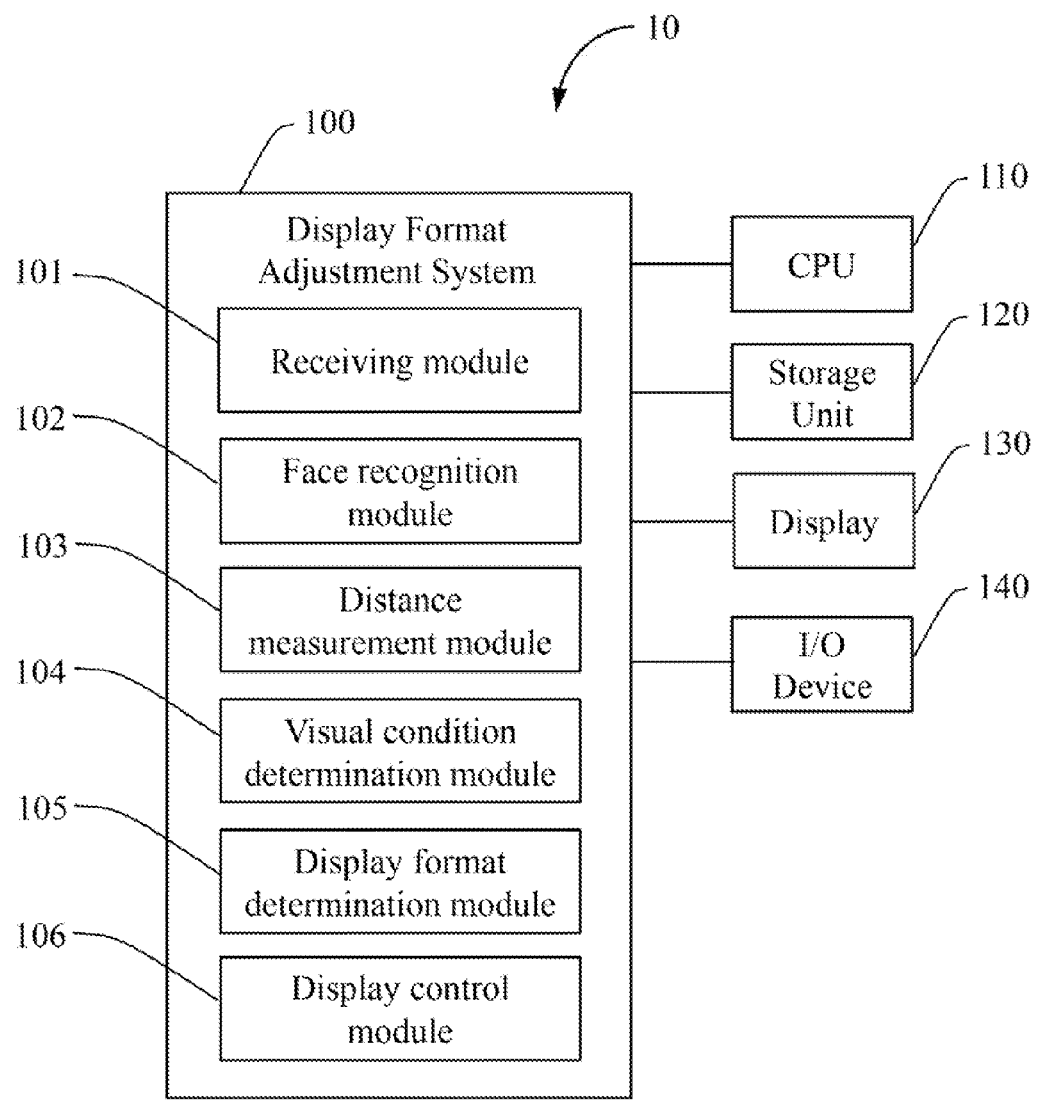
FIG. 2 is a schematic diagram of one embodiment of the function modules of the display format adjustment system of FIG. 1.

FIG. 2 illustrates a schematic diagram of one embodiment of the function modules of the display format adjustment system 100. In one embodiment, the display format adjustment system 100 includes a receiving module 101, a face recognition module 102, a distance measurement module 103, a visual condition determination module 104, a display format determination module 105, and a display control module 106. Each of the modules 101-106 may be a software program including one or more computerized instructions that are stored in the storage unit 120 and executed by the CPU 110.

The receiving module 101 may receive content for display in a first display format. The content may include text and/or images. The first display format may include text font size information and/or image size information for defining the appearance and style of the content when it is displayed on the display 130. The text font size may include the height and the width, such as 18×18 pixels, to define the size of a text font. The image size may include the height and the width, such as 320×480 pixels, to define the size of an image.

The face recognition module 102 may recognize face of a viewer in front of the display 130. The face recognition module 102 may capture an image of the viewer using a camera and identify the face of the viewer through the captured image.

The distance measurement module 103 is installed in the electronic device 10 for measuring a view distance between the face of the viewer and the display 130. The distance measurement module 103 may use a variety of distance detecting technologies such as ultrasonic, infrared and lasers.

The visual condition determination module 104 may determine a visual condition of the viewer. In one embodiment, the visual condition determination module 104 may receive a visual acuity index input by the viewer. In another embodiment, the visual condition determination module 104 may display a visual acuity test chart on the display. Referring to FIG. 3, an example of a visual acuity test chart (a Snellen chart) is illustrated. The Snellen chart is displayed with eleven lines of block letters. The row with the smallest characters that can be read accurately indicates the visual acuity of the viewer. The number identifying the smallest row can serve as the visual acuity index of the viewer. The visual condition determination module 104 may determine the visual acuity index by testing the viewer using the visual acuity test chart. According to the determined visual acuity index, the visual condition determination module 104 may determine a minimal size. The minimal size is a size of which a visual element smaller than is unrecognizable for the viewer. The minimal size may include a height and a width. For example, the visual condition determination module 104 may determine that the visual acuity index of the viewer is "6" and the minimal size for "6" is 18×18 pixels, according to the visual acuity index.

The display format determination module 105 may determine a second display format based on the first display format and the visual condition of the viewer as determined by the visual condition determination module 104. The display format determination module 105 may obtain size(s) of the second display format by using an equation as follows:

$$\begin{cases} S_2 = S_1, & (S_{min} \geq S_{va}) \\ S_2 = S_1 * (S_{va}/S_{min}), & (S_{min} < S_{va}) \end{cases}$$

where $S_2$ represents the size of the second display format, $S_1$ represents the size of the first display format, $S_{va}$ represent the minimal size relative to the visual acuity index, $S_{min}$ represents the size of the smallest visual element defined by the first display format.

When the second display format has been determined, the display control module 106 may display the content in the second display format on the display 130.

In one embodiment, the distance measurement module 103 may measure and record a first view distance between the face of the viewer and the display 130 when the visual condition determination module 104 determines the visual condition of the viewer. When the viewer moves nearer to or farther away from the display 130, the distance measurement module 103 may measure and record a second view distance between the face of the viewer and the display 130.

The display format determination module 105 may determine a third display format based on the second display format and a relation between the first view distance and the second view distance. The display format determination module 105 may obtain size(s) of the third display format by using an equation as follows:

$$\begin{cases} S_3 = S_2, & (D_2 < D_1) \\ S_3 = S_2 * (D_2/D_1), & (D_2 \geq D_1) \end{cases}$$

where $S_3$ represents the size of the third display format, $S_2$ represents the size of the second display format, $D_2$ represents the second view distance, and $D_1$ represents the first view distance.

When the third display format has been determined, the display control module 106 may display the content in the third display format on the display 130.

Figure 4:
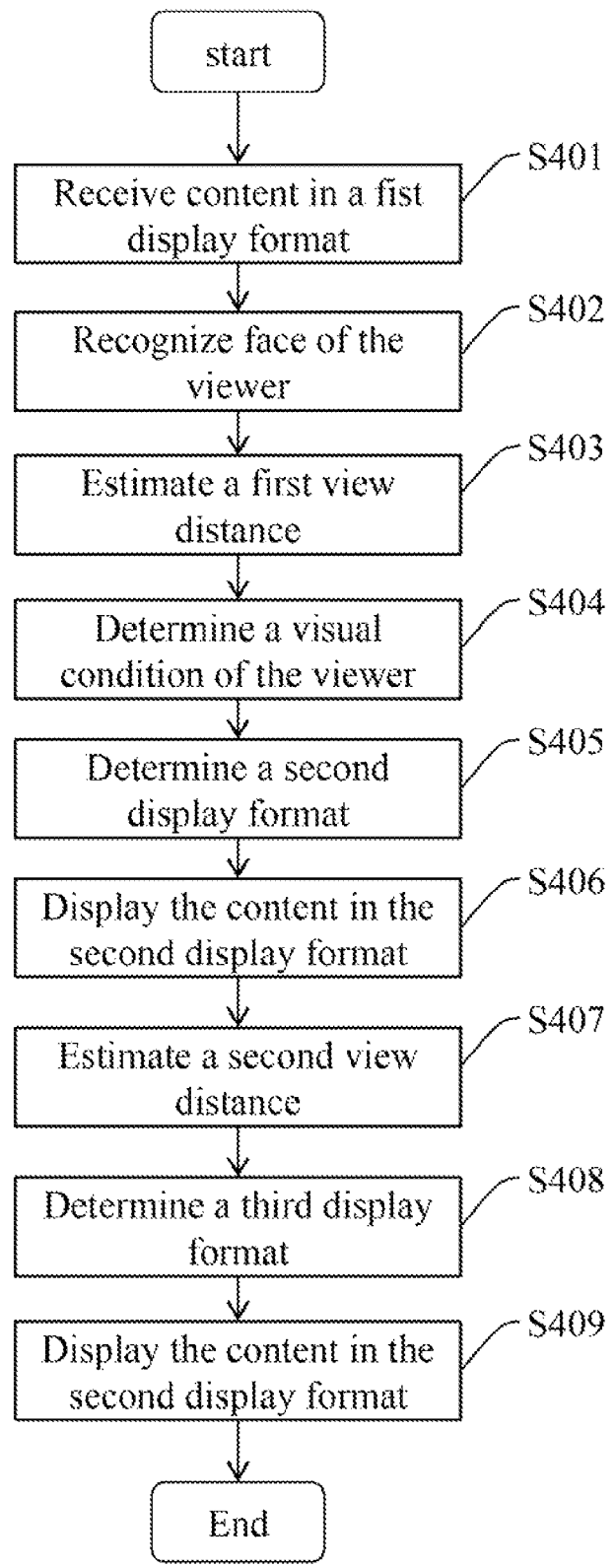
FIG. 4 is an operational flow diagram representing one embodiment of a method for adjusting display format using the display format adjustment system of FIG. 1.

FIG. 4 is a flowchart illustrating one embodiment of a method for adjusting display format using the display format adjustment system of FIG. 1. The method may include the following steps.

In step S401, the receiving module 101 receives content for display in a first display format.

In step S402, the face recognition module 102 recognizes face of a viewer in front of the display 130.

In step S403, the distance measurement module 103 measures and records a first view distance between the face of the viewer and the display 130.

In step S404, the visual condition determination module 104 determines a visual condition of the viewer. The visual condition determination module 104 displays a visual acuity test chart on the display 130, determines a visual acuity index for the viewer by testing the viewer using the visual acuity test chart. According to the determined visual acuity index, the visual condition determination module 104 determines a minimal size. The minimal size is a size of which a visual element smaller than is unrecognizable for the viewer.

In step S405, the display format determination module 105 determines a second display format based on the first display format and the visual condition of the viewer. The display format determination module 105 obtains size(s) of the second display format by using an equation as follows:

$$\begin{cases} S_2 = S_1, & (S_{min} \geq S_{va}) \\ S_2 = S_1 * (S_{va}/S_{min}), & (S_{min} < S_{va}) \end{cases}$$

where $S_2$ represents the size of the second display format, $S_1$ represents the size of the first display format, $S_{va}$ represent the minimal size relative to the visual acuity index, and $S_{min}$ represents the size of the smallest visual element defined by the first display format.

In step S406, the display control module 106 displays the content in the second display format on the display 130.

In step S407, the distance measurement module 103 measures a second view distance between the face of the viewer and the display 130.

In step S408, the display format determination module 105 determines a third display format based on the second display format and a relation between the first view distance and the second view distance. The display format determination module 105 obtains size(s) of the third display format by using an equation as follows:

$$\begin{cases} S_3 = S_2, & (D_2 < D_1) \\ S_3 = S_2 * (D_2/D_1), & (D_2 \geq D_1) \end{cases}$$

where $S_3$ represents the size of the third display format, $S_2$ represents size of the second display format, $D_2$ represents the second view distance, and $D_1$ represents the first view distance.

In step S409, the display control module 106 displays the content in the third display format on the display 130.

It is to be understood, however, that even though numerous characteristics and advantages have been set forth in the foregoing description of embodiments, together with details of the structures and functions of the embodiments, the disclosure is illustrative only and changes may be made in detail, especially in matters of shape, size, and arrangement of parts within the principles of the disclosure to the full extent indicated by the broad general meaning of the terms in which the appended claims are expressed.

Depending on the embodiment, certain steps or methods described may be removed, others may be added, and the sequence of steps may be altered. It is also to be understood that the description and the claims drawn for or in relation to a method may include some indication in reference to certain steps. However, any indication used is only to be viewed for identification purposes and not as a suggestion as to an order for the steps.

What is claimed is:

1. A computer-implemented method for adjusting display format in an electronic device, the method comprising:
   receiving content for display in a first display format at the electronic device;
   measuring a first distance between a viewer and a display of the electronic device;
   determining a visual condition of the viewer at the first distance;
   determining a second display format based on the first display format and the visual condition of the viewer; and
   displaying the content in the second display format on the display;
   measuring a second distance between the viewer and the display after the content has been displayed in the second display format on the display;
   determining a third display format based on the second display format and a relation between the first distance and the second distance; and
   displaying the content in the third display format on the display.

2. The method of claim 1, wherein the display formats comprise text font size information.

3. The method of claim 1, wherein the display formats comprise image size information.

4. The method of claim 1, wherein the step of determining the third display format comprises obtaining size of the third display format by using an equation as follows:

$$\begin{cases} S_3 = S_2, & (D_2 < D_1) \\ S_3 = S_2 * (D_2/D_1), & (D_2 \geq D_1) \end{cases}$$

where $S_3$ represents the size of the third display format, $S_2$ represents size of the second display format, $D_2$ represents the second distance, $D_1$ represents the first distance.

5. The method of claim 1, wherein the step of determining the visual condition of the viewer comprises:
   displaying a visual acuity test chart on the display;
   determining a visual acuity index by testing the viewer using the visual acuity test chart; and
   determining a minimal size relative to the visual acuity index, wherein the minimal size is a size of which a visual element smaller than is unrecognizable for the viewer.

6. The method of claim 5, wherein the step of determining the second display format comprises obtaining size of the second display format by using an equation as follows:

$$\begin{cases} S_2 = S_1, & (S_{min} \geq S_{va}) \\ S_2 = S_1 * (S_{va}/S_{min}), & (S_{min} < S_{va}) \end{cases}$$

where $S_2$ represents the size of the second display format, $S_1$ represents size of the first display format, $S_{va}$ represent the minimal size relative to the visual acuity index, $S_{min}$ represents size of the smallest visual element defined by the first display format.

7. The method of claim 1, further comprising recognizing face of the viewer by a camera of the electronic device, wherein the first distance and the second distance are measured between the face of the viewer and the display.

8. A system for adjusting display format in an electronic device, the system comprising:
   a receiving module configured for receiving content for display in a first display format;
   a distance measurement module configured for measuring a first distance between a viewer and a display of the electronic device;
   a visual condition determination module configured for determining a visual condition of the viewer at the first distance;
   a display format determination module configured for determining a second display format based on the first display format and the visual condition of the viewer; and
   a display control module configured for displaying the content in the second display format on the display;
   wherein the distance measurement module is further configured for measuring a second distance between the viewer and the display after the content has been displayed in the second display format on the display, the display format determination module is further configured for determining a third display format based on the second display format and a relation between the first distance and the second distance; and the display control module is further configured for displaying the content in the third display format on the display.

9. The system of claim 8, wherein the display formats comprise text font size information.

10. The system of claim 8, wherein the display formats comprise image size information.

11. The system of claim 8, wherein the display format determination module is configured for obtaining size of the third display format by using an equation as follows:

$$\begin{cases} S_3 = S_2, & (D_2 < D_1) \\ S_3 = S_2 * (D_2/D_1), & (D_2 \geq D_1) \end{cases},$$

where $S_3$ represents the size of the third display format, $S_2$ represents size of the second display format, $D_2$ represents the second distance, $D_1$ represents the first distance.

12. The system of claim 8, wherein the visual condition determination module is configured for displaying a visual acuity test chart on the display, determining a visual acuity index by testing the viewer using the visual acuity test chart, and determining a minimal size relative to the visual acuity index, where the minimal size is a size of which a visual element smaller than is unrecognizable for the viewer.

13. The system of claim 12, wherein the second display format determination module is configured for obtaining size of the second display format by using an equation as follows:

$$\begin{cases} S_2 = S_1 & (S_{min} \geq S_{va}) \\ S_2 = S_1 * (S_{va}/S_{min}), & (S_{min} < S_{va}) \end{cases}$$

where $S_2$ represents the size of the second display format, $S_1$ represents size of the first display format, $S_{va}$, represent the minimal size relative to the visual acuity index, $S_{min}$ represents size of the smallest visual element defined by the first display format.

14. The system of claim 8, further comprising a face recognition module adapted to recognize face of the viewer by a camera of the electronic device, wherein the distance measurement module is configured for measuring distance between the face of the viewer and the display.

* * * * *